United States Patent [19]

Bistline, Jr. et al.

[11] Patent Number: 4,663,353
[45] Date of Patent: May 5, 1987

[54] ANTIBACTERIAL FATTY ANILIDES

[75] Inventors: Raymond G. Bistline, Jr.; Elmer W. Maurer, both of Wyndmoor; Frank D. Smith, Upper Black Eddie; Warner M. Linfield, Oreland, all of Pa.

[73] Assignee: The United States of America as represented by the Secretary of Agriculture, Washington, D.C.

[21] Appl. No.: 233,242

[22] Filed: Feb. 10, 1981

Related U.S. Application Data

[63] Continuation-in-part of Ser. No. 18,084, Mar. 6, 1979, abandoned.

[51] Int. Cl.$^4$ .............................................. A61K 31/165
[52] U.S. Cl. ...................................... 514/617; 514/858
[58] Field of Search ............. 424/324; 260/404, 404.5; 514/617

[56] References Cited

U.S. PATENT DOCUMENTS

| | | | |
|---|---|---|---|
| 2,978,465 | 4/1961 | Jerchel | 424/324 X |
| 3,037,058 | 5/1962 | Bluestone et al. | 424/324 X |
| 3,418,345 | 12/1968 | Baker | 424/324 X |
| 3,426,049 | 2/1969 | Baker | 424/324 |
| 3,551,462 | 12/1970 | Seki et al. | 424/324 |
| 3,555,091 | 1/1971 | Benoit-Guyod et al. | 424/324 |
| 3,816,092 | 6/1974 | Wilson et al. | 71/118 |

FOREIGN PATENT DOCUMENTS

| | | | |
|---|---|---|---|
| 545118 | 8/1957 | Canada | 424/324 |
| 1301M | 5/1962 | France | 424/324 |
| 8585 | 4/1969 | Japan | 424/324 |
| 29155 | 8/1971 | Japan | 424/324 |
| 1360001 | 7/1974 | United Kingdom | 424/324 |

OTHER PUBLICATIONS

Beaver et al., JACS, 1957, vol. 79, pp. 1236–1245.

*Primary Examiner*—Dale R. Ore
*Attorney, Agent, or Firm*—M. Howard Silverstein; David G. McConnell

[57] ABSTRACT

Certain substituted fatty analides were found to exhibit antimicrobial activity.

2 Claims, No Drawings

ANTIBACTERIAL FATTY ANILIDES

CROSS REFERENCES TO RELATED APPLICATION

This application is a continuation-in-part of application Ser. No. 18,084, filed Mar. 6, 1979, now abandoned.

BACKGROUND OF THE INVENTION

1. Field of the Invention

This invention relates to certain substituted fatty anilides which have exhibited antimicrobial activity. More particularly, this invention relates to anilides in which the aniline nucleus contains one or two substituents selected from the group consisting of halogen, nitro, and hydroxy.

2. Description of Art

U.S. Pat. No. 3,418,345 discloses certain halonitroanilides possessing microbiological activity. It also discloses that discovery of activity among these certain compounds is totally unexpected because tests run on compounds closely related in structure including various homologs and chain and position isomers were either completely inactive or required high concentrations to control bacterial growth.

Beaver et al, JACS 79, 1236 (1957) disclosed certain carbanilides which exhibited bacteriostatic properties.

Anilides have also been disclosed as food preservatives, fungicides, and as having other biological activity.

SUMMARY OF THE INVENTION

An object of this invention is to provide certain substituted fatty anilides which exhibit antibacterial activity.

Another object of this invention is to provide substituted fatty anilides which do not lose their antibacterial activity in the presence of soap or when formulated in an aqueous solution containing soap.

According to the present invention the above objects are accomplished by compounds of the general formula

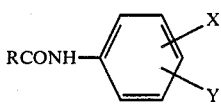

wherein R is alkyl having from 5 to 11 carbon atoms and X and Y are individuall chlorine, hydrogen, nitro, or hydroxyl.

More specifically, the objects are accomplished by compounds of the above general formula wherein, when both X and Y are chlorine, R has 5, 7, 8, or 10 carbon atoms; when X is a nitro group and Y is hydrogen, R has from 7 to 9 carbon atoms; when both X and Y are nitro groups, R has 8 carbon atoms; when X is hydroxyl and Y is a nitro group, R has from 7 to 9 carbon atoms; and when X is hydroxyl and Y is chlorine, R has 5, 8, 9, or 11 carbon atoms. These compounds provide effective bacteriostatic activity at concentrations of from 0.1 to 1.0 ppm when formulated in aqueous or aqueous-ethanol solutions or in aqueous solutions containing soap.

DETAILED DESCRIPTION OF THE INVENTION

The compounds of this invention are prepared by conventional laboratory procedures involving the reaction of acyl chlorides with aniline and substituted anilines. The acyl component of the anilide may contain 4 to 12 carbon atoms. The amide nitrogen is derived from substituted anilines in the following group: 3,4-dichloroaniline, m-nitroaniline, p-nitroaniline, 5-chloro-2-hydroxy aniline and 2-amino-4-nitrophenol.

The antimicrobial activity of the fatty anilides has been established in vitro and, as will be apparent to those skilled in the art of growth inhibition of bacteria, the compounds may be used by themselves or may be formulated with soaps or surface active agents, with or without diluents such as water, to give liquid, viscous, or solid products. A wide variety of extending agents is operable, the only significant requirement being that the diluent or extender be inert with respect to the compound involved.

The compounds of this invention have been found to possess useful and unexpected antimicrobial activity in inhibiting the growth of bacteria. To illustrate bacteriostatic properties the following test procedure was employed: 1% stock solutions were prepared by dissolving 100 mg of compound in 10 ml of water. If necessary, 95% ethanol was used to help dissolve the compound in water. The stock solutions were serially diluted by successively pipetting 2 ml of solution into 18 ml of sterile nutrient agar to obtain 1000, 100, 10, 1 and 0.1 ppm concentrations of the compound. The agar was poured into sterile Petri dishes, allowed to harden, then inoculated with one drop of a 24 hour culture of test microorganism Staphylococcus aureus in nutrient broth. The inoculated samples were incubated at 37° C. for 48 hours and examined for the presence or absence of bacterial growth. Compounds active in the range of 1–10 ppm were retested for activity as aqueous compositions containing 1000 ppm soap.

The invention will be more fully understood by reference to the following examples. These examples, however, are given for the purpose of illustration only and are not to be construed as limiting the scope of the present invention in any manner.

EXAMPLE 1

3,4-Dichloroaniline, 13.7 g (0.084 mole), is dissolved in 200 ml dichloroethane, containing 25 ml pyridine. The solution is stirred at room temperature while nonanoyl chloride, 14.6 g (0.086 mole), is added slowly. The solution is stirred two hours. Excess pyridine is removed by washing the product with 4N hydrochloric acid. A crude product is crystallized from 95% ethanol. There is obtained N-(3,4-dichlorophenyl) nonanamide, a white crystalline solid, (M.P. 68.5–69.0%). Analysis shows 4.52% nitrogen and 23.26% chlorine as against calculated values of 4.63% and 23.48% respectively for $C_{15}H_{21}Cl_2NO$.

N-(3,4-Dichlorophenyl) amides of butanoic (M.P. 76.5–77.)), hexanoic (M.P. 74.0–74.5), octanoic (M.P. 39.0–39.5), 10-undecenoic (M.P. 58.0–58.5), dodecanoic (M.P. 78.0–78.5) and hexadecanoic acids (M.P. 79.5–80.0) are prepared according to the above description.

EXAMPLE 2 m-Nitroaniline, 10.0 g (0.072 mole), is dissolved in 150 ml dichloroethane, containing 25 ml pyridine. The solution is stirred at room temperature while nonanoyl chloride, 12.9 g (0.073 mole), is added slowly. The solution is stirred for 2 hours. Excess pyridine is removed by washing the product with 4N hydrochloric acid. The product is then passed through a florisil column and crystallized at −20° C. There is obtained N-(3-nitrophenyl) nonanamide (M.P. 63.0°-63.5° C.). Analysis shows 9.88% nitrogen as against a calculated value of 10.06% for $C_{15}H_{21}N_2O_3$.

N-(3-Nitrophenyl) amides of hexanoic (M.P. 62.5–63.0), octanoic (M.P. 65.0–65.5), decanoic (M.P. 72.0–72.5) and dodecanoic acids (M.P. 80–80.5), are prepared, according to the above description.

EXAMPLE 3 p-Nitroaniline, 13.0 g (0.094 mole), is dissolved in 200 ml dichloroethane, containing 25 ml pyridine. The solution is stirred at 50° C. while nonanoylchloride, 16.5 g (0.094 mole), is added slowly. The solution is stirred for 2 hours. Excess pyridine is removed by washing the product with 4N hydrochloric acid. The product is then passed through a florisil column and crystallized at −20° C. There is obtained N-(4-nitrophenyl) nonanamide, (M.P. 76.0°–76.5°). Analysis shows 9.91% nitrogen as against a calculated value of 10.06% for $C_{15}H_{21}N_2O_3$.

N-(4-Nitrophenyl) amides of hexanoic (M.P. 66.5–67.0), octanoic (M.P. 77.0–77.5), decanoic (M.P. 73.5–74.0%) and dodecanoic acids (M.P. 78.5–79.0), are prepared according to the above description.

EXAMPLE 4

3,5-Dinitroaniline, 10.0 g (0.055 mole), is dissolved in 200 ml dichloroethane, containing 25 ml pyridine. The solution is stirred at room temperature while nonanoyl chloride, 10.3 g (0.058 mole), is added slowly. The solution is stirred for 2 hours. Excess pyridine is removed by washing the product with 4N hydrochloric acid. The product is obtained by crystallization at −20° C. and recrystallized from 95% ethanol. There is obtained N-(3,5-Dinitrophenyl) nonanamide (M.P. 72.5°–73.0° C.). Analysis shows 12.69% nitrogen as against a calculated value of 12.61% for $C_{15}H_{21}N_3O_5$.

EXAMPLE 5

2-Amino-4-nitrophenol, 10.8 g (0.070 mole), is dissolved in 100 ml distilled water, containing 25 ml pyridine. The solution is stirred at room temperature while nonanoykl chloride, 12.4 g (0.072 mole), is added slowly. The solution is stirred for 2 hours. 100 ml dichloroethane is then added to isolate the product. Excess pyridine is removed by washing with 4N hydrochloric acid. The product is obtained by crystallization at −20° C. There is obtained N-(2-hydroxy-5-nitrophenyl) nonanamide (M.P. 140°–141° C.). Analyis shows 9.45% nitrogen as against a calculated value of 9.52% for $C_{15}H_{22}N_2O_3$.

The N-(2-Hydroxy-5-nitrophenyl) amides of hexanoic (M.P. 136.0–137.0) octanoic (M.P. 127.0–128.0) decanoic (M.P. 126.5–127.0) and dodecanoic (M.P. 110.0–111.0) fatty acids are prepared according to the above description.

EXAMPLE 6

4-chloro-3-nitroaniline, 10.1 g (0.058 mole), is dissolved in 100 ml dichloroethane, containing 25 ml pyridine. The solution is stirred at room temperature while nonanoylchloride, 10.5 g (0.067 mole), is added slowly. The solution is stirred for 2 hours. Excess pyridine is removed by washing the product with 4N hydrochloric acid. The product is then passed through a florisil column. The product does not crystallize from dichloroethane which was removed. The product was crystallized from 80% ethanol. There is obtained N-(4-Chloro-3-nitrophenyl) nonanamide (M.P. 44.5–45.0). Analysis shows 8.9% nitrogen and 11.26% chlorine as against calculated values of 8.96% and 11.33% respectively for $C_{15}H_{21}ClN_2O_3$.

The N-4-Chloro-3-nitrophenyl) amides of hexanoic (M.P. 27°–28°), octanoic (M.P. 34.0–35.0) decanoic (M.P. 58.0–58.5) and dodecanoic (M.P. 66.5–67.0) fatty acids are prepared according to the above description.

EXAMPLE 7

5-Chloro-2-hydroxy aniline, 10.3 g (0.072 mole), is dissolved in 200 ml dichloroethane, containing 25 ml pyridine. The solution is stirred at 70° C. while nonanoyl chloride is added slowly. The solution is stirred for 2 hours. Excess pyridine is removed by washing the product with 4N hydrochloric acid. The product is then passed through a florisil column and crystallized at −20°. There is obtained N-(5-chloro-2-hydroxyphenyl) nonanamide (M.P. 93.5–94.0). Analysis shows 4.94% nitrogen and 12.53% chlorine as against calculated values of 49.4% and 12.49% respectively, for $C_{15}H_{22}ClNO_2$.

The N-(5-chloro-2-hydroxyphenyl) amides of hexanoic (M.P. 97.5–98.0), octanoic (M.P. 94.0–94.5) decanoic (M.P. 90.0–90.5) and dodecanoic (M.P. 73.5–74.0) acids are prepared according to the above description.

Antimicrobial properties of compositions the compounds of this invention formulated in an aqueous medium and of the compounds in the presence of soap are shown in Table 1. The compounds are stated as being tested in the presence of soap to emphasize the fact that the soap does not materially affect in an adverse manner the efficacy of the compounds. However, the compounds are actually formulated in an aqueous solution which contains soap at a concentration of 1000 p.p.m. In order to prepare compositions having the desired concentrations of compound, ethanol was used to help solubilize those compounds which were not readily soluble in water. The amount of ethanol used to affect solubility and prepare the compositions was minimal and it was determined that the ethanol had neither deleterious nor enhancing effect on the antibacterial activity. As can be seen the compounds that are useful as bacteriostatic agents are those in which X and Y of the general formula

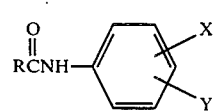

are the following groups attached to the aromatic ring at the noted positions:

| X | Y | |
|---|---|---|
| 3-Cl | 4-Cl | N—(3,4-dichloro) |
| 3-NO₂ | H | N—(3-nitro-) |
| 4-NO₂ | H | N—(4-nitro-) |
| 3-NO₂ | 5-NO₂ | N—(3,5-dinitro-) |
| 2-OH | 5-NO₂ | N—(2-hydroxy-5-nitro-) |
| 3-NO₂ | 4-CL | N—(3-nitro-4-chloro-) |
| 2-OH | 5-Cl | N—(2-hydroxy-5-chloro-) |

In order to demonstrate that the aforesaid microbiological activity is unexpected, tests were also run with closely related compounds including various homologs and position isomers. Of the many closely related compounds tested, the following nonamides are cited:

Nonananilide
N-Methyl-N-phenyl nonanamide
Diphenyl nonanamide
N-(2-Methylphenyl) nonanamide
N-(3-Methylphenyl) nonanamide
N-(4-Methylphenyl) nonanamide
N-(2,6-Dimethylphenyl) nonanamide
N-(3,4-Dimethylphenyl) nonanamide
N-(2-Hydroxyphenyl) nonanamide
N-(3-Hydroxyphenyl) nonanamide
N-(4-Hydroxyphenyl) nonanamide
N-(4-cyclopropylphenyl) nonanamide
N-(4-Trifluoromethylphenyl) nonanamide
N-(2-chlorophenyl) nonanamide
N-(3-chlorophenyl) nonanamide
N-(4-chlorophenyl) nonanamide
N-(2,3-Dichlorophenyl) nonanamide
N-(2,4-Dichlorophenyl) nonamide
N-(2,5-Dichlorophenyl) nonanamide
N-(2,6-Dichlorophenyl) nonanamide
N-(3,4-Dichlorophenylmethyl) nonanamide
N-(2-Nitrophenyl) nonanamide
N-(2,4-Dinitrophenyl) nonanamide
N-(2,6-Dinitrophenyl) nonanamide
N-(4-Hydroxy-3-nitrophenyl) nonanamide
N-(2-Chloro-4-nitrophenyl) nonanamide
N-(2-Chloro-5-nitrophenyl) nonanamide
N-(4-Chloro-2-nitrophenyl) nonanamide
Sodium[3,4-dichlorophenyl]α-sulfo nonanamide All of the above compounds were found to be either completely inactive or to control the growth of bacteria only at concentrations at least 10 times greater than the effective concentrations of the most closely related counterparts of this invention.

As previously noted, another very strong indication that the art is unpredictable is found in U.S. Pat. No. 3,418,345, in which Baker discloses that he found that certain halonitroanilides possessed microbiological activity. However, he also found that a number of closely related compounds including various homologs and chain and position isomers were completely inactive or required very high concentrations to exhibit microbiological activity. With this knowledge, one would certainly hesitate to try to predict which halonitroanilides might exhibit microbiological activity and such a prediction would be immeasurably more difficult when, as is found in the composition of this invention, the substituents for X and Y in the general formula are for other than a combination of halogen and a nitro group.

To further illustrate the unexpectedness of the desirable properties of the compounds of this invention, a few other compounds in which the minimal inhibitory concentration required to inhibit the growth of *Stephylococcus aureus* was very high are shown in Table 2.

TABLE 1

Minimum Concentration of Compound Required to Inhibit Growth of *Staphylococcus Aureus*

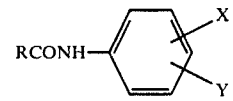

| | Compound | | Concentration | |
|---|---|---|---|---|
| R | X | Y | Compound ppm | Compound with 1000 ppm soap ppm |
| | position and group | | | |
| C₅H₁₁ | 3-Cl | 4-Cl | 1.0 | 1.0ᵃ |
| C₇H₁₅ | 3-Cl | 4-Cl | 0.1 | 1.0ᵃ |
| C₈H₁₇ | 3-Cl | 4-Cl | 0.1 | 1.0ᵃ |
| C₇H₁₅ | 3-NO₂ | H | 1.0ᵃ | 1.0ᵃ |
| C₈H₁₇ | 3-NO₂ | H | 0.1 | 10.0 |
| C₉H₁₉ | 3-NO₂ | H | 1.0 | 10.0 |
| C₇H₁₅ | 4-NO₂ | H | 0.1 | 0.1ᵃ |
| C₈H₁₇ | 4-NO₂ | H | 0.1 | 0.1ᵃ |
| C₉H₁₉ | 4-NO₂ | H | 0.1 | 0.1ᵃ |
| C₈H₁₇ | 3-NO₂ | 5-NO₂ | 0.1 | 0.1ᵃ |
| C₇H₁₅ | 2-OH | 5-NO₂ | 0.1 | 0.1ᵃ |
| C₈H₁₇ | 2-OH | 5-NO₂ | 0.1 | 0.1 |
| C₉H₁₉ | 2-OH | 5-NO₂ | 0.1 | 0.1ᵃ |
| C₅H₁₁ | 3-NO₂ | 4-Cl | 0.1 | 1.0 |
| C₇H₁₅ | 3-NO₂ | 4-Cl | 0.1 | 0.1 |
| C₈H₁₇ | 3-NO₂ | 4-Cl | 0.1 | 0.1ᵃ |
| C₉H₁₉ | 3-NO₂ | 4-Cl | 0.1 | 1.0ᵃ |
| C₅H₁₁ | 2-OH | 5-Cl | 0.1 | 1.0ᵃ |
| C₇H₁₅ | 2-OH | 5-Cl | 10.0 | 1.0ᵃ |
| C₈H₁₇ | 2-OH | 5-Cl | 0.1 | 1.0ᵃ |
| C₉H₁₉ | 2-OH | 5-Cl | 0.1 | 1.0ᵃ |
| C₁₁H₂₃ | 2-OH | 5-Cl | 1.0 | 1.0ᵃ |
| C₁₀H₁₉ | 3-Cl | 4-Cl | 0.1 | 1.0ᵃ |

ᵃpartial inhibition

TABLE 2

Minimum Concentration of Compound Required to Inhibit Growth of *Staphylococcus Aureus*

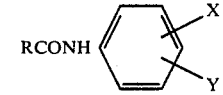

| | Compound | | Concentration |
|---|---|---|---|
| R | X | Y | ppm |
| | position and group | | |
| C₃H₇ | 3-Cl | 4-Cl | 100 |
| C₅H₁₁ | 3-NO₂ | H | 100 |
| C₅H₁₁ | 4-NO₂ | H | 100 |
| C₉H₁₉ | 4-Cl | H | >1000 |
| C₁₁H₂₃ | 3-Cl | 4-Cl | 1000 |
| C₁₁H₂₃ | 3-NO₂ | H | >1000 |
| C₁₁H₂₃ | 3-NO₂ | 4-Cl | >1000 |
| C₁₁H₂₃ | 4-NO₂ | H | >1000 |
| C₁₁H₂₃ | 2-OH | 5-NO₂ | 1000 |
| C₁₅H₃₁ | 3-Cl | 4-Cl | >1000 |

We claim:

1. A method of inhibiting the growth of *Staphylococcus aureus* by applying to said organisms an effective bacteriostatic amount of a bacteriostatically effective concentration of a composition comprised of (a) a fatty anilide having the general formula RCONH 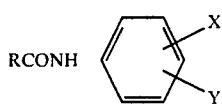

in which R is alkyl having from 5 to 11 carbon atoms and X and Y are individually chlorine, hydrogen, nitro or hydroxyl in the following combinations, when both X and Y are chlorine in the 3, 4 positions, R has 5, 7, 8 or 10 carbon atoms; when X is a nitro group in the 3 or 4 position, and Y is hydrogen, R has 7, 8 or 9 carbon atoms; when both X and Y are nitro groups in the 3, 5 positions, R has 8 carbon atoms; when X is hydroxyl in the 2 position, and Y is a nitro group in the 5 position, R has 7, 8 or 9 carbon atoms; and when X is hydroxyl in the 2 position, and Y is chlorine in the 5 position, R has 5, 8, 9 or 11 carbon atoms, and (b) an aqueous carrier containing an anilide solubilizing amount of ethanol, said anilide being present at a concentration of from 0.1 to 1.0 ppm.

2. The method of claim 1 in which the aqueous carrier contains soap at a concentration of 1000 ppm.

* * * * *